United States Patent
Li et al.

(10) Patent No.: US 9,149,467 B2
(45) Date of Patent: Oct. 6, 2015

(54) SUSTAINED-RELEASE COMPOSITION CONTAINING TETRAHYDROPYRIDO[4,3-B]INDOLE DERIVATIVES AND PREPARATION OF THE DERIVATIVES

(75) Inventors: Song Li, Beijing (CN); Wu Zhong, Beijing (CN); Zhibing Zheng, Beijing (CN); Junhai Xiao, Beijing (CN); Bing Li, Beijing (CN); Yunde Xie, Beijing (CN); Xinbo Zhou, Beijing (CN)

(73) Assignee: Institute of Pharmacology and Toxicology Academy of Military Medical Science P.L.A. China, Beijing (CN)

( * ) Notice: Subject to any disclaimer, the term of this patent is extended or adjusted under 35 U.S.C. 154(b) by 0 days.

(21) Appl. No.: 13/263,790

(22) PCT Filed: Mar. 29, 2010

(86) PCT No.: PCT/CN2010/000396
§ 371 (c)(1),
(2), (4) Date: Oct. 27, 2011

(87) PCT Pub. No.: WO2010/115342
PCT Pub. Date: Oct. 14, 2010

(65) Prior Publication Data
US 2012/0122914 A1    May 17, 2012

(30) Foreign Application Priority Data
Apr. 10, 2009  (CN) .......................... 2009 1 0131626

(51) Int. Cl.
*A01N 43/42* (2006.01)
*A61K 31/44* (2006.01)
*A61K 9/16* (2006.01)
*A61K 9/20* (2006.01)
*C07D 471/04* (2006.01)

(52) U.S. Cl.
CPC ............... *A61K 31/44* (2013.01); *A61K 9/1641* (2013.01); *A61K 9/2031* (2013.01); *A61K 9/2077* (2013.01); *C07D 471/04* (2013.01)

(58) Field of Classification Search
CPC ... A61K 31/44; A61K 9/1641; A61K 9/2031; A61K 9/2077; C07D 471/04
See application file for complete search history.

(56) References Cited

U.S. PATENT DOCUMENTS 5,849,240 A * 12/1998 Miller et al. .................. 264/460
2001/0019725 A1 * 9/2001 Miller et al. .................. 424/489

FOREIGN PATENT DOCUMENTS

| EP | 2236160 A2 | 10/2010 |
|---|---|---|
| WO | 2006086229 A1 | 8/2006 |
| WO | 2008051599 A2 | 5/2008 |
| WO | 2008069963 A1 | 6/2008 |
| WO | 2008123796 A2 | 10/2008 |
| WO | 2009/017836 A1 | 2/2009 |

OTHER PUBLICATIONS

Extended Supplementary European Search Report for Application No. 10761171.7 dated Mar. 7, 2012.
Kost et al., "Chemistry of Indole. XXXIII. Pyridylethylation of the NH group of indole compounds," Chemistry of Heterocyclic Compounds, vol. 9, No. 2, Feb. 1, 1973, pp. 191-195.
Extended Supplementary European Search Report for Application No. 12197026.3 dated Mar. 15, 2013.

* cited by examiner

Primary Examiner — Wu-Cheng Winston Shen
Assistant Examiner — Jean Cornet
(74) Attorney, Agent, or Firm — Banner & Witcoff, Ltd.

(57) ABSTRACT

The present invention relates to a sustained-release composition containing 2,3,4,5-tetrahydro-2,8-dimethyl-5-[2-(6-methyl-3-pyridyl)ethyl]-1H-pyrido[4,3-b]indole or a pharmaceutically acceptable salt thereof as an active ingredient, preparation thereof and the compound. The composition is suitable for oral administration by one time per day, and achieves the peak plasma concentration at 1.0 to 3 hours after oral administration. The composition is suitable for manufacturing a medicament for treatment of cognitive dysfunction syndrome, Alzheimer's disease, Parkinson's disease, Huntington's disease, or senile dementia.

4 Claims, No Drawings

SUSTAINED-RELEASE COMPOSITION CONTAINING TETRAHYDROPYRIDO[4,3-B]INDOLE DERIVATIVES AND PREPARATION OF THE DERIVATIVES

TECHNICAL FIELD

The present relates to a sustained-release composition and a process for preparing the same. More specifically, the present invention relates to a sustained-release unit dosage form for oral administration comprising 2,3,4,5-tetrahydro-2,8-dimethyl-5-[2-(6-methyl-3-pyridyl)ethyl]-1H-pyrido[4,3-b]indole (compound of Formula I, Dimebolin) or a pharmaceutically acceptable salt thereof as an active ingredient, and the pharmaceutically acceptable salt is most preferably 2,3,4,5-tetrahydro-2,8-dimethyl-5-[2-(6-methyl-3-pyridyl)ethyl]-1H-pyrido[4,3-b]indole dihydrochloride (Dimebon) (compound of Formula II).

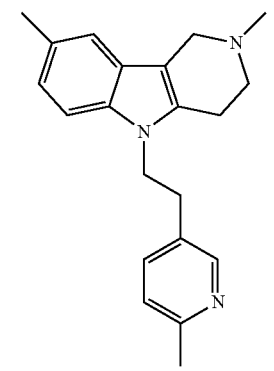

Formula I

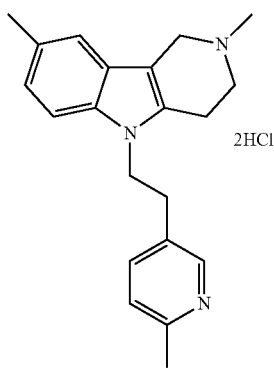

Formula II

2HCl

The present invention further relates in general to a process for preparing the sustained-release composition such as a sustained-release oral dosage form, which oral dosage from is preferably sustained-release granules/multiparticulates and compressed multiparticulates, for example, multiparticulates with a diameter ranging from 0.1-0.3 mm; and the process of the present invention is capable of providing multiparticulates in a high yield.

BACKGROUND ART

In 1969, it was reported that 2,3,4,5-tetrahydro-2,8-dimethyl-5-[2-(6-methyl-3-pyridyl)ethyl]-1H-pyrido[4,3-b]indole (compound of Formula I, Dimebolin) and 2,3,4,5-tetrahydro-2,8-dimethyl-5-[2-(6-methyl-3-pyridyl)ethyl]-1H-pyrido[4,3-b]indole dihydrochloride (Dimebon) had antihistamine and antiallergic effects (U.S. Pat. No. 3,484,449). In 1983, it was marketed in the former Soviet Union as an antiallergic agent for clinic use (Farmakologiia i Toksikologiia 46 (4): 27-29); and the protective effects of the compound on nerves and the effects of the compound for improving cognitive dysfunction had been studied (Vestnik Rossiiskoi Akademii Meditsinskikh Nauk (9): 13-17).

In recent years, some studies indicate that Dimebolin has a bioactivity by oral administration. It has been shown that this product inhibits the death of brain cells in pre-clinical trials on Alzheimer's disease and Huntington's disease, can enhance the cognition of healthy people and patients with never degenerative diseases, and can treat cognitive dysfunction syndrome in dogs (US08036400). Studies indicate that Dimebolin has potential therapeutic effects on the abovementioned and other never degenerative diseases (Annals of the New York Academy of Sciences (939): 425-435).

Some researches also show that Dimebolin has a significant therapeutic effect in the patients with Alzheimer's disease. In 2000, a research conducted in an animal model of Alzheimer's disease in Russia indicated that Dimebolin had a significant therapeutic effect on Alzheimer's disease (Bulletin of Experimental Biology and Medicine 129 (6): 544-546). Recently, the results of a phase II human clinical trial for initial 6 months have showed that Dimebolin has a significant effect for improving patients with Alzheimer's disease as compared to the placebo, and a phase III double blind clinical trial is performing now (Antihistamine Shows Promise in Treating Alzheimer's", New York Times (2007-06-11)).

2,3,4,5-tetrahydro-2,8-dimethyl-5-[2-(6-methyl-3-pyridyl)ethyl]-1H-pyrido-[4,3-b]indole (compound of Formula I) and 2,3,4,5-tetrahydro-2,8-dimethyl-5-[2-(6-methyl-3-pyridyl)ethyl]-1H-pyrido[4,3-b]indole dihydrochloride (Dimebolin, Dimebon) are novel compounds capable of treating never degenerative diseases such as cognitive dysfunction syndrome, Alzheimer's disease, Parkinson's disease, Huntington's disease, senile dementia, etc., and there are two preparations thereof for human clinical trials, i.e., preparations respectively containing 5 mg and 20 mg of 2,3,4,5-tetrahydro-2,8-dimethyl-5-[2-(6-methyl-3-pyridyl)ethyl]-1H-pyrido[4,3-b]indole (compound of Formula I), in which the recommended usage of the 20 mg preparation is three times per day, i.e., the activity of the preparation can keep for 8 hours, so that it should be taken three times per day.

However, although Dimebolin is a compound capable of treating never degenerative diseases such as cognitive dysfunction syndrome, Alzheimer's disease, Parkinson's disease, Huntington's disease, senile dementia, etc., the current preparation that has to be taken three times per day is not favorable for the treatment of patients with never degenerative diseases such as cognitive dysfunction syndrome, Alzheimer's disease, Parkinson's disease, Huntington's disease, senile dementia, etc., because the patients may hardly remember too many times of drug administration and may very likely forget the administration due to their diseases; and in the meantime, drug administration for several times is also inconvenient for those accompanying and attending the patients.

The object of the present invention is to provide a sustained-release unit dosage form for oral administration comprising 2,3,4,5-tetrahydro-2,8-dimethyl-5-[2-(6-methyl-3-pyridyl)ethyl]-1H-pyrido[4,3-b]indole (compound of Formula I, Dimebolin) or a pharmaceutically acceptable salt thereof as an active ingredient, and the pharmaceutically acceptable salt is most preferably 2,3,4,5-tetrahydro-2,8-dimethyl-5-[2-(6-methyl-3-pyridyl)ethyl]-1H-pyrido[4,3-b]

indole dihydrochloride (Dimebon). The dosage form has an effective activity duration of 24 hours or more, and thus is suitable for administration by one time per day, thereby being greatly convenient to patients with never degenerative diseases such as cognitive dysfunction syndrome, Alzheimer's disease, Parkinson's disease, Huntington's disease, senile dementia, etc. and those accompanying and attending the patients, avoiding weakening therapeutic effect in the patients caused by missing administration, and facilitating the treatment and recovery of the patients.

DISCLOSURES OF THE INVENTION

The present invention provides a sustained-release unit dosage form for oral administration comprising 2,3,4,5-tetrahydro-2,8-dimethyl-5-[2-(6-methyl-3-pyridyl)ethyl]-1H-pyrido[4,3-b]indole (compound of Formula I) or a pharmaceutically acceptable salt thereof as an active ingredient, and the pharmaceutically acceptable salt is most preferably 2,3,4,5-tetrahydro-2,8-dimethyl-5-[2-(6-methyl-3-pyridyl)ethyl]-1H-pyrido[4,3-b]indole dihydrochloride (Dimebon). The dosage form has an effective activity duration of 24 hours or more, and thus is suitable for administration by one time per day.

The first aspect of the present invention relates to a sustained-release composition, comprising, relative to the weight of the sustained-release composition, 10-60% of 2,3,4,5-tetrahydro-2,8-dimethyl-5-[2-(6-methyl-3-pyridyl)ethyl]-1H-pyrido[4,3-b]indole (Formula I) or a pharmaceutically acceptable salt thereof, a hydrophobic meltable carrier or diluent selected from hydrogenated vegetable oil (commonly called "non-dairy creamer"), hydrogenated castor oil, beeswax, carrauba wax, microcrystalline wax or glyceryl monostearate, 0.01-20% of a release regulating component selected from polyethylene glycol having a molecular weight of 1000-20000, poloxamer, lactose or dicalcium phosphate, and an optional conventional tablet excipient.

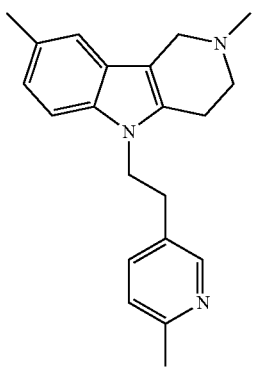

F.I

Another aspect of the present invention relates to a process for preparing a sustained-release composition, comprising mixing 2,3,4,5-tetrahydro-2,8-dimethyl-5-[2-(6-methyl-3-pyridyl)ethyl]-1H-pyrido[4,3-b]indole or a pharmaceutically acceptable salt thereof, a hydrophobic meltable carrier or diluent, a hydrophilic release regulating component, and an optional conventional tablet excipient.

According to the invention, in the sustained-release composition or its unit dosage form, 2,3,4,5-tetrahydro-2,8-dimethyl-5-[2-(6-methyl-3-pyridyl)ethyl]-1H-pyrido[4,3-b]indole or a pharmaceutically acceptable salt thereof has a weight amount of 10%-60%, preferably 40-60%; or 15-60 mg as expressed in the dose of 2,3,4,5-tetrahydro-2,8-dimethyl-5-[2-(6-methyl-3-pyridyl)ethyl]-1H-pyrido[4,3-b]indole.

In the present invention, the hydrophobic meltable carrier or diluent is natural or synthetic hydrophobic substances such as waxes or oils, for example, hydrogenated vegetable oil or hydrogenated castor oil, and has a melting point of 35-100° C., preferably 45-90° C.

In the present invention, when the hydrophilic release regulating component is a hydrophilic fusible substance, it is appropriately polyethylene glycol or poloxamer, when being a particulate substance, it is appropriately a pharmaceutically acceptable substance, such as dicalcium phosphate or lactose. The polyethylene glycol preferably has a molecular weight of 1000-20000, and the amount of the release regulating component is 0.01-20%, preferably 0.01-2% in relative to the total weight of the composition.

In the present invention, the conventional tablet excipient is generally a pharmaceutically acceptable excipient for tablet, such as purified talc, magnesium stearate, etc.

According to the present invention, the sustained-release composition of the present invention is used in unit dosage form for oral administration, and the unit dosage form can be granules or tablets, in which the granules can be used in the form of capsules.

The inventors of the present invention found that the sustained-release preparation comprising 2,3,4,5-tetrahydro-2,8-dimethyl-5-[2-(6-methyl-3-pyridyl)ethyl]-1H-pyrido[4,3-b]indole (compound of Formula I) or a pharmaceutically acceptable salt thereof achieved an effective therapeutical activity for a time period of 24 hours or more, after the intragastric administration of the preparation in rabbits, the in vivo peak plasma concentration was quickly arrived, i.e., the in vivo peak plasma concentration was arrived within 1-3 hours, preferably 1-2 hours after the administration.

The unit dosage form according to the present invention should contain a sufficient amount of 2,3,4,5-tetrahydro-2,8-dimethyl-5-[2-(6-methyl-3-pyridyl)ethyl]-1H-pyrido[4,3-b]indole (compound of Formula I) or a pharmaceutically acceptable salt thereof as an active ingredient to achieve a therapeutic activity that can be sustained for at least 24 hours. The amount of 2,3,4,5-tetrahydro-2,8-dimethyl-5-[2-(6-methyl-3-pyridyl)ethyl]-1H-pyrido[4,3-b]indole (compound of Formula I) or a pharmaceutically acceptable salt thereof in any specific dosage form depends on some variables, including (1) estimated number of dosage form to be taken at any one time; and (2) estimated dose for any specific patient. For convenience, the unit dosage form according to the present invention will contain 15-60 mg of 2,3,4,5-tetrahydro-2,8-dimethyl-5-[2-(6-methyl-3-pyridyl)ethyl]-1H-pyrido[4,3-b]indole (expressed in 2,3,4,5-tetrahydro-2,8-dimethyl-5-[2-(6-methyl-3-pyridyl)ethyl]-1H-pyrido[4,3-b]indole), hence, for example, a typical unit dosage form according to the present invention contains 18.4-73.7 mg of Dimebon.

According to another aspect of the present invention, the features of the pharmaceutical preparation containing an effective amount of 2,3,4,5-tetrahydro-2,8-dimethyl-5-[2-(6-methyl-3-pyridyl)ethyl]-1H-pyrido[4,3-b]indole or a pharmaceutically acceptable salt thereof and having potency sustained for at least 24 hours lie in: the $W_{50}$ for 2,3,4,5-tetrahydro-2,8-dimethyl-5-[2-(6-methyl-3-pyridyl)ethyl]-1H-pyrido[4,3-b]indole is between 2 and 12 hours, preferably 2 to 5 hours.

The parameter $W_{50}$ is defined as a width of plasma profile at 50% Cmax, i.e., the time of duration that plasma concentration is equal to or greater than 50% of the peak concentration. This parameter is determined by linear interpolation of the observed data, which represents a time difference between the first ascending cross point and the last descending cross point.

According to the present invention, the features of the pharmaceutical preparation containing an effective amount of 2,3,4,5-tetrahydro-2,8-dimethyl-5-[2-(6-methyl-3-pyridyl)ethyl]-1H-pyrido[4,3-b]indole or a pharmaceutically acceptable salt thereof and having potency sustained for at least 24 hours lie in: the $W_{50}$ for 2,3,4,5-tetrahydro-2,8-dimethyl-5-[2-(6-methyl-3-pyridyl)ethyl]-1H-pyrido[4,3-b]indole is between 2 and 12 hours, preferably 2 and 5 hours, and preferably the $t_{max}$ occurs between 1 and 3 hours, preferably 1 and 2 hours after the administration.

The $C_{maxs}$ of the preparation of the present invention depends on dose, for example, when a preferable embodiment containing 60 mg of 2,3,4,5-tetrahydro-2,8-dimethyl-5-[2-(6-methyl-3-pyridyl)ethyl]-1H-pyrido[4,3-b]indole is administrated in unit dosage form, which is characterized in that the intragastric administration in rabbits shows the $C_{maxs}$ of 2,3,4,5-tetrahydro-2,8-dimethyl-5-[2-(6-methyl-3-pyridyl)ethyl]-1H-pyrido[4,3-b]indole ranges in 1.5-4 µg/ml.

According to the present invention, in order to achieve the desired peak plasma concentration of 2,3,4,5-tetrahydro-2,8-dimethyl-5-[2-(6-methyl-3-pyridyl)ethyl]-1H-pyrido[4,3-b]indole and provide effective activity for a time period of at least 24 hours, the preparation should have the following in vitro release profile (rotating basket method) measured at 100 rpm and 37° C. in 900 ml of aqueous buffer solution (pH 6.5) containing 0.05% w/v Tween 80.

| after test (h) | %, released dimebolin |
|---|---|
| 2 | 5-30 |
| 4 | 15-50 |
| 6 | 20-50 |
| 12 | 35-75 |
| 18 | 45-100 |
| 24 | 60-100 |

The composition of the present invention can be provided in many forms, for example, tablets, granules such as capsules containing granules, spheres or pills. The composition generally comprises 2,3,4,5-tetrahydro-2,8-dimethyl-5-[2-(6-methyl-3-pyridyl)ethyl]-1H-pyrido[4,3-b]indole or a pharmaceutically acceptable salt thereof as an active ingredient, and a hydrophobic meltable carrier or diluent capable of controlling the release of the active component.

According to the present invention, the preferable embodiments of unit dosage form include capsules filled with multiparticulates, the multiparticulates mainly comprise the active component, the meltable carrier or diluent, and comprises a hydrophilic release regulating component.

Specifically, the multiparticulates are preferably manufactured by the following method, primarily comprising: preparing a mixture of a dry active component and a hydrophobic meltable carrier or diluent, then mechanically processing the mixture in a high speed blender at a certain speed, providing sufficient energy to co-melt or soften the fusible substance so as to form multiparticulates containing the active component. The obtained mutiparticulates are screened and cooled to obtain mutiparticulates having particle size of 0.1-3.0 mm, preferably 0.25-2.0 mm. This preferable method is suitable for industrial production of unit dosage form containing 2,3,4,5-tetrahydro-2,8-dimethyl-5-[2-(6-methyl-3-pyridyl)ethyl]-1H-pyrido[4,3-b]indole or a pharmaceutically acceptable salt thereof.

The weight proportion of the active component in the composition can vary in a relatively broad scope, for example, can be 10-60%, preferably 40-60%.

The present invention further relates to a process for preparing sustained-release multiparticulates containing 2,3,4,5-tetrahydro-2,8-dimethyl-5-[2-(6-methyl-3-pyridyl)ethyl]-1H-pyrido[4,3-b]indole or a pharmaceutically acceptable salt thereof, which comprises:

1) in a high speed blender, mechanically processing a mixture comprising granular 2,3,4,5-tetrahydro-2,8-dimethyl-5-[2-(6-methyl-3-pyridyl)ethyl]-1H-pyrido[4,3-b]indole or a pharmaceutically acceptable salt thereof and a granular hydrophobic meltable carrier or diluent with a melting point of 35-150° C., such as 35-100° C., and an optional release regulating component by stirring, and providing energy to melt or soften the carrier or diluent so as to form an aggregate; wherein the release regulating component comprises a hydrophilic fusible substance, or a granular soluble or insoluble organic or inorganic substance;

2) pulverizing the relatively large aggregate to obtain control seeds; and 3) continuing the mechanical processing, simultaneously adding a low percentage of the carrier and diluent; and 4) repeating the step 3) and possible step 2) once or many times, for example, up to 6 times.

The aforementioned "mechanically processing by stirring at a certain speed" generally means the stirring speed is 20-200 rpm; the providing energy in "providing energy to melt or soften the carrier or diluent" means heating the granular active component to a temperature of 35-150° C.

The method can be used to obtain multiparticulates in a high yield (exceed 80%), the obtain multiparticulates have desired particle size and desired in vitro release rate, and the release rate is uniform. It is surprising that the plasma concentration initial peak of the product in preferable form has an activity duration period of 24 hours.

The obtained multiparticulates can be screened by passing through sieves to remove excessively large or excessively small particles, then processed by, for example, filling into hard capsules to obtain the desired unit dosage form containing a desired dose of the active substance.

The obtained granules can be used for preparing unit dosage forms such as tablets or capsules according to the known methods in the art.

In the present invention, the amount of the active component allows the content of 2,3,4,5-tetrahydro-2,8-dimethyl-5-[2-(6-methyl-3-pyridyl)ethyl]-1H-pyrido[4,3-b]indole or a pharmaceutically acceptable salt thereof in the multiparticulates between 10-60 (W/W) %, or between 10-45 (W/W) % for a low dose product.

In the above method, the amount of all of the drug in combination with the most of the used hydrophobic meltable carrier or diluent is preferably 25-45% (w/w), more preferably 30-40% (w/w), relative to the total amount of components added during the whole production process.

In order to produce the tablet of the present invention, the multiparticulates as prepared above and a desired excipient can be mixed by a conventional method, and the resultant mixture is tableted by a tableting device with desired size according to a conventional tableting method.

Another aspect of the present invention relates to a process for preparing a compound of Formula I, comprising:

a) preparing 2-methyl-5-acetylpyridine from methyl 6-methylnicotinate;

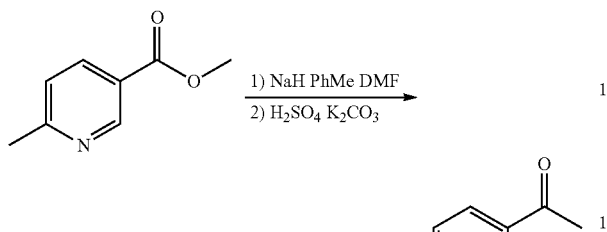

b) reacting 2-methyl-5-acetylpyridine with morpholine to obtain 2-(6-methylpyridin-3-yl)morpholinylethylthione;

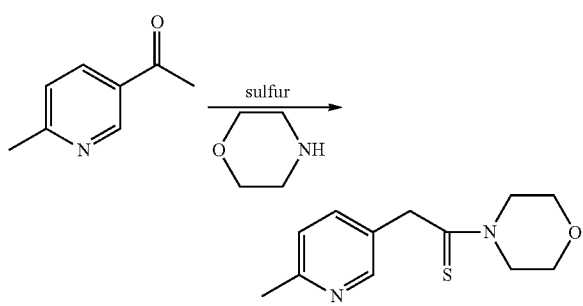

c) preparing 2-methyl-5-pyridinylacetic acid from 2-(6-methylpyridin-3-yl)morpholinylethylthione at alkaline condition;

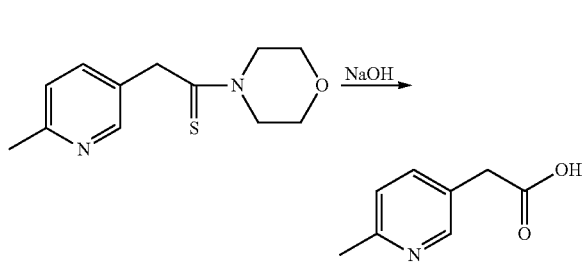

d) reacting 2-methyl-5-pyridinylacetic acid with p-toluidine to obtain 2-(6-methylpyridin-3-yl)N-p-tolylamide;

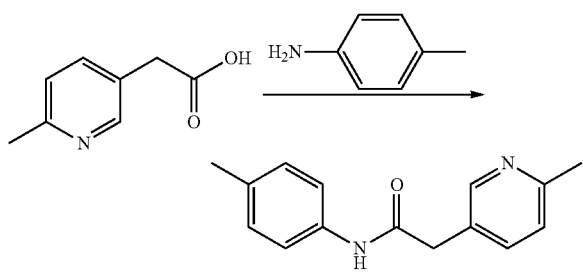

e) reacting 2-(6-methylpyridin-3-yl)N-p-tolylamide with sodium borohydride to obtain 5-(2-p-tolylaminoethyl)-2-methylpyridine;

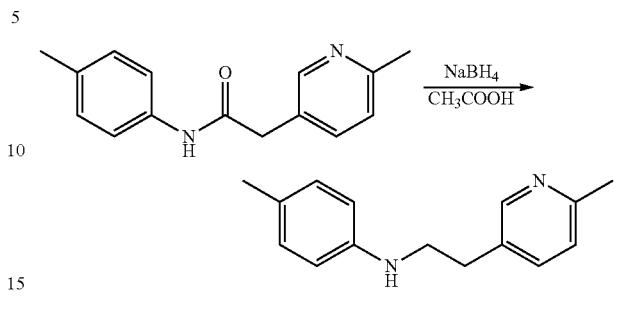

f) subjecting 5-(2-p-tolylaminoethyl)-2-methylpyridine to diazotization to obtain 2-methyl-5-(N-nitroso-2-p-tolylaminoethyl)pyridine;

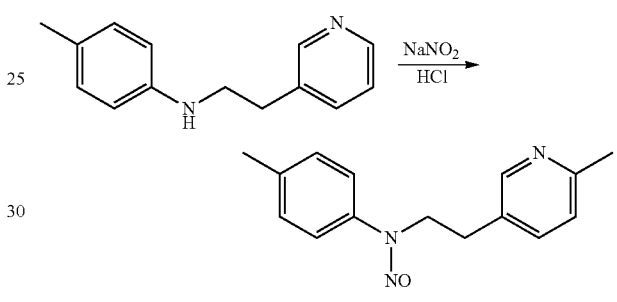

g) reacting 2-methyl-5-(N-nitroso-2-p-tolylaminoethyl)pyridine with sodium thiosulfate to obtain 2-methyl-5-(N-amino-2-p-tolylaminoethyl)pyridine;

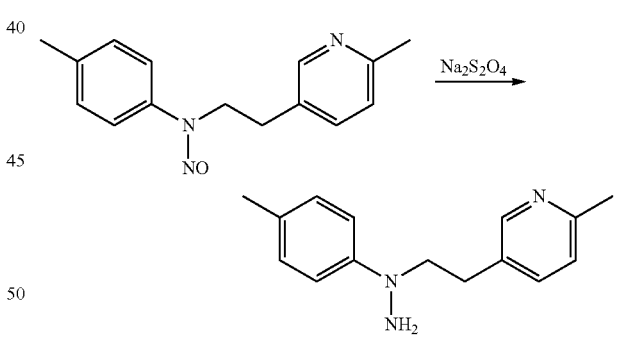

h) preparing 2,3,4,5-tetrahydro-2,8-dimethyl-5-[2-(6-methyl-3-pyridyl)ethyl]-1H-pyrido[4,3-b]indole or dihydrochloride thereof from 2-methyl-5-(N-amino-2-p-tolylaminoethyl)pyridine;

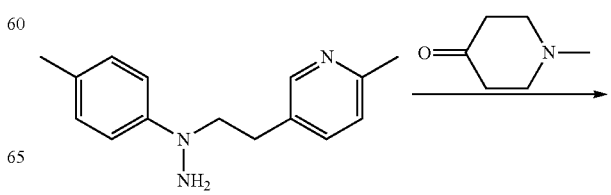

-continued

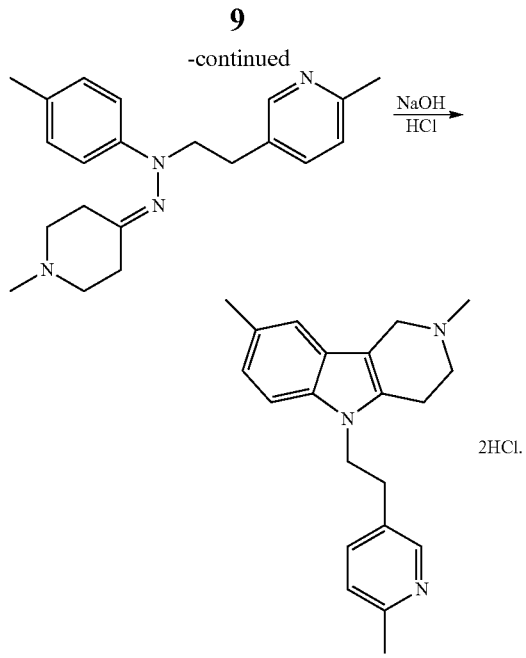

Another aspect of the present invention relates to a use of a sustained-release pharmaceutical preparation containing at least one compound of Formula I or a pharmaceutically acceptable salt thereof such as the compound of Formula II as an active ingredient for treatment of cognitive dysfunction syndrome, Alzheimer's disease, Parkinson's disease, Huntington's disease, senile dementia, etc.

In order to sufficiently understand the present invention, the following examples are provided for explanation.

CONCRETE MODES FOR CARRYING OUT THE INVENTION

Example 1

Preparation of 2-methyl-5-acetylpyridine 50 g of methyl 6-methylnicotinate was dissolved in 200 ml of ethyl acetate; 60% NaH 26.5 g, toluene 400 ml and DMF 34 ml were added to a three-necked bottle, 10% methyl 6-methylnicotinate ethyl acetate solution 20 ml was added, heated to 80° C., stirred for 0.5 h. To the reaction bottle, the residual methyl 6-methylnicotinate ethyl acetate solution was added dropwise slowly within about 1.5 h. After addition, the reaction was conducted at 80° C. for 8 h. The reaction stopped, cooled to room temperature. 300 ml of water was added to the reaction bottle, skimmed, the water layer was extracted with ethyl acetate three times, 200 ml per time. All ethyl acetate layers were combined, distillated at a reduced pressure to evaporate ethyl acetate, then 10% $H_2SO_4$ aqueous solution 400 ml was added, heated to 110° C., refluxed for 2 h. The reaction was then stopped, cooled to room temperature. Solid $K_2CO_3$ was used to adjust PH to 9, suction filtration was performed, the filter cake was washed with ethyl acetate. The filtrate was extracted with ethyl acetate four times, combined and rotary evaporated to dry, to obtain 35 g of 2-methyl-5-acetylpyridine, yield was about 65%.

MS(EI) 135.1 (M+)

Example 2

Preparation of 2-(6-methylpyridin-3-yl)morpholinylethylthione 2-methyl-5-acetylpyridine 35 g, sulfur 7.5 g, morpholine 60 ml were placed in a 250 ml round bottom flask, heated to 110° C., reacted under refluxing for 7 h. The reaction stopped after 7 h, cooled to room temperature. Water 100 ml was added for dilution, ethyl acetate was used for extraction for many times, combined, ethyl acetate was rotary evaporated out. The obtained solid mixture was recrystallized using ethyl acetate to obtain brown needle solid 2-(6-methylpyridin-3-yl)morpholinylethylthione 25 g.

MS(EI) 236.1 (M+)

Example 3

Preparation of 2-methyl-5-pyridinylacetic acid 2-(6-methylpyridin-3-yl)morpholinylethylthione 25 g was dissolved in 200 ml of ethanol, then 60% NaOH aqueous solution (21 g NaOH dissolved in 25 ml water) was added, heated to 80° C., refluxed for 17 h. The reaction stopped, cooled to room temperature, rotary evaporated out solvent. A small amount of water was added for dissolution, adjusted with concentrated hydrochloric acid to reach a PH of 2, suction filtrated out insoluble substance, the filtrate was extracted with ethyl ether twice, the ethyl ether layers were combined and washed with water once. The water layers were collected for standby use. Rotary evaporated out solvent water, placed in vacuum drying oven and dried for 24 h to obtain 2-methylpyridinylacetic acid 11 g, yield was about 70%.

$^1$H-NMR (400 MHz, DMSO-$d_6$) δ 2.43 (3H, s, $CH_3$); 3.57 (2H, s, $CH_2$); 7.17-7.19 (1H, d, ArH); 7.53-7.56 (1H, dd, ArH); 8.30-8.31 (1H, d, ArH); 12.42 (1H, s, COOH).

Example 4

Preparation of 2-(6-methylpyridin-3-yl)N-p-tolylamide 2-methylpyridinylacetic acid was dissolved in 150 ml of DMF, added with DIEA 40 ml, p-toluidine 10.2 g, HOBt 18 g, and stirred for 15 min, then added with EDC.HCl 21 g, after addition, the reaction was performed at room temperature for 12 h. Then, water 800 ml was added for dilution, stirred, insoluble solid appeared, after stirring for 2 h, suction filtrated, washed with water to obtain off-white powder solid, dried to obtain 2-(6-methylpyridin-3-yl)N-p-tolylamide 12 g, yield was about 68%.

$^1$H-NMR (400 MHz, DMSO-$d_6$) δ 2.19 (3H, s, $CH_3$); 2.39 (3H, s, $CH_3$); 3.56 (2H, s, $CH_2$); 7.06-7.04 (2H, d, ArH); 7.15-7.17 (1H, d, ArH); 7.40-7.42 (2H, d, ArH); 7.55-7.57 (1H, dd, ArH); 8.32 (1H, d, ArH); 10.07 (1H, s, NH).

Example 5

Preparation of 5-(2-p-methylphenylaminoethyl)-2-methylpyridine

To a three-necked bottle, dioxane 150 ml was added, cooled with ice-water to 10° C., then added with the above-prepared 2-(6-methylpyridin-3-yl)N-p-tolylamide and $NaBH_4$, stirred for 10 min. Kept at 10° C., added dropwise with glacial acetic acid dioxane solution (10 ml glacial acetic acid was dissolved in 100 ml of dioxane). Reaction time was about 1 h. A great quantity of hydrogen gas generated. After dropwise addition, the temperature was elevated slowly to 105° C., reaction was performed under refluxing for 2.5 h.

The reaction stopped, cooled to room temperature, 300 ml of water was added for dilution. Yellow deposition precipitated, suction filtrated, washed with water, recrystallized using ethyl acetate/ethanol mixture solution to obtain off-white powdery solid, dried to obtain 5-(2-p-methylphenylaminoethyl)-2-methylpyridine 4.5 g, yield was about 40%.

$^1$H-NMR (400 MHz, DMSO-d$_6$) δ2.14 (3H, s, CH$_3$); 2.58 (3H, s, CH$_3$); 2.85-2.88 (2H, t, CH$_2$); 3.22-3.26 (2H, t, CH$_2$); 5.48 (1H, s, NH); 6.49-6.51 (2H, d, ArH); 6.88-6.90 (2H, d, ArH); 7.55-7.57 (1H, d, ArH); 7.93-7.95 (1H, dd, ArH); 8.57 (1H, d, ArH).

Example 6

Preparation of 2-methyl-5-(N-nitroso-2-p-methylphenylaminoethyl)pyridine

To a three-necked bottle, 5-(2-p-methylphenylaminoethyl)-2-methylpyridine 4.5 g and 2N HCl 200 ml was added, heated to 30° C. and stirred to complete dissolution, then cooled with ice-water bath to 0-5° C., added dropwise with NaNO$_2$ aqueous solution (13.8 g of NaNO$_2$ dissolved in 50 ml of water). After dropwise addition, the temperature was elevated and the reaction was performed at room temperature for 1 h. To the reaction liquor, saturated NaHCO$_3$ solution was slowly added dropwise until no gas generated. A great quantity of solid appeared, stirred for 1 h, suction filtrated, washed with water to obtain light yellow solid powder, dried and weighed to obtain 2-methyl-5-(N-nitroso-2-p-methylphenylaminoethyl)pyridine 4.3 g. Yield was about 85%.

$^1$H-NMR (400 MHz, DMSO-d$_6$) δ2.36 (3H, s, CH$_3$); 2.40 (3H, s, CH$_3$); 2.70-2.74 (2H, t, CH$_2$); 4.24-4.28 (2H, t, CH$_2$); 7.12-7.14 (1H, d, ArH); 7.31-7.33 (2H, d, ArH); 7.43-7.46 (2H, d, ArH); 7.46-7.50 (1H, dd, ArH); 8.20-8.21 (1H, d, ArH).

Example 7

Preparation of 2-methyl-5-(N-amino-2-p-methylphenylaminoethyl)pyridine

To a three-necked bottle, 20% NaOH aqueous solution and ethanol were added, then added with 2-methyl-5-(N-nitroso-2-p-benzylaminoethyl)pyridine, protected with nitrogen gas, condensing tube. Heated to 60° C. and stirred for 0.5 h. Na$_2$S$_2$O$_4$ was added, under the protection of nitrogen gas, the reaction was performed at 60° C. for 12 h. The reaction stopped, cooled to room temperature. The reaction liquor was extracted with ethyl ether three times. All ethyl ether layers were combined, dried with anhydrous sodium sulfate overnight. The ether layer was evaporated to dryness to obtain a crude product, the crude product was purified and separated by chromatography using petroleum ether/ethyl acetate (1/2) as eluent to obtain light yellow solid 2-methyl-5-(N-amino-2-p-tolylaminoethyl)pyridine 1.4 g. Yield was about 35%.

$^1$H-NMR (400 MHz, DMSO-d$_6$) δ2.17 (3H, s, CH$_3$); 2.41 (3H, s, CH$_3$); 2.80-2.84 (2H, t, CH$_2$); 3.46-3.49 (2H, t, CH$_2$); 4.22-4.23 (2H, s, NH$_2$); 6.87-6.89 (2H, d, ArH); 6.90-6.96 (2H, d, ArH); 7.15-7.17 (1H, d, ArH); 7.57-7.59 (1H, dd, ArH); 8.34 (1H, d, ArH)

Example 8

Preparation of 2,3,4,5-tetrahydro-2,8-dimethyl-5-[2-(6-methyl-3-pyridyl)ethyl]-1H-pyrido[4,3-b]indole and dihydrochloride thereof 2-methyl-5-(N-amino-2-p-methylphenylaminoethyl)pyridine 1.4 and N-methyl-4-piperidone 0.8 g were added, toluene 100 ml was added for dissolution, heated to 120° C., reacted under refluxing for 24 h. The reaction stopped, cooled, evaporated out solvent toluene. To the residue, 5.3N hydrochloric acid ethanol 20 ml was added dropwise to dissolve all the residue, then heated to 80° C., and reacted under refluxing for 1.5 h.

The reaction stopped, diluted with water, neutralized with 6N NaOH to pH14. The reaction liquor was extracted with ethyl ether three times, all ethyl ether layers were combined, washed with water solution once and saturated NaCl solution twice, the obtained ethyl ether layer was vacuum evaporated to obtain a crude product. The obtained crude product was recrystallized with ethyl acetate, filtrated and dried to obtain 2,3,4,5-tetrahydro-2,8-dimethyl-5-[2-(6-methyl-3-pyridyl)ethyl]-1H-pyrido[4,3-b]indole (compound of Formula I) 1.2 g. Yield was about 65%.

The obtained compound of Formula I was dissolved in 5 ml of methanol, slowly added dropwise with saturated hydrochloric acid methanol solution until the solution had a pH of 2-3. The acidic solution was stirred at 0° C. for 2 h, suction filtrated to obtain a crude product, the crude product was dried. The obtained crude product was recrystallized with a mixture solution of ethanol and ethyl ether to obtain 2,3,4,5-tetrahydro-2,8-dimethyl-5-[2-(6-methyl-3-pyridyl)ethyl]-1H-pyrido[4,3-b]indole dihydrochloride (compound of Formula II) 1 g, yield was about 83%.

$^1$H-NMR (400 MHz, DMSO-d$_6$) δ2.36 (3H, s, CH$_3$); 2.39 (3H, s, CH$_3$); 2.45 (3H, s, CH$_3$); 2.56 (2H, s, CH$_2$); 2.72 (2H, s, CH$_2$); 2.88-2.91 (2H, t, CH$_2$); 3.58 (2H, s, CH$_2$); 4.20-4.23 (2H, t, CH$_2$); 6.88-6.90 (1H, d, ArH); 7.10 (1H, s, ArH); 7.12 (1H, s, ArH); 7.35-7.58 (1H, d, ArH); 7.35-7.3 (1H, dd, ArH); 8.14 (1H, d, ArH)

Examples 9-11

The granules of the formulas as shown in Table 2 were prepared according to the following steps:
1) placing the components a to c into a tank of a blender (or an equivalent device) equipped with speed changing blades for mixing and tableting;
2) mixing the components under about 150-350 rpm, and simultaneously heated until the material in the tank is aggregated;
3) classifying the aggregated material to obtain sustained-release seeds;
4) warming and mixing the classified material in the tank of the blender, simultaneously adding the component d until uniform granules with a desired size profile are obtained in a yield of higher than 80%;
5) discharging the granules from the blender and passing through sieves to collect granules between 0.5 mm sieve and 2 mm sieves.

TABLE 2

| Examples/components | 9 | 10 | 11 |
|---|---|---|---|
| a. compound of formula I (wt %) | 55.0 | 52.0 | 53.5 |
| b. hydrogenated vegetable oil (wt %) | 34.95 | 33.17 | 34.00 |

TABLE 2-continued

| Examples/components | 9 | 10 | 11 |
|---|---|---|---|
| c. polyethylene glycol 6000 (wt %) | 0.05 | 0.047 | 0.05 |
| d. hydrogenated vegetable oil (wt %) | 10.0 | 14.79 | 12.54 |
| Yield (%) | 90.5 | 88.5 | 92.5 |

Example 12

The steps of Example 11 were repeated, with the following changes: conveying the classified granules to a cool tank of the blender, then adding the component d and mixing, heating by jacket and microwaves during mixing.

The in vitro release rates of Examples 9-12 were measured by a improved rotating basket method at 100 rpm and 37° C. in 900 ml of aqueous buffer solution (pH 6.5) containing 0.05% w/v Tween 80. For each of the products of Examples 9-12, 6 granule samples were tested, and each sample contained total 60 mg of 2,3,4,5-tetrahydro-2,8-dimethyl-5-[2-(6-methyl-3-pyridyl)ethyl]-1H-pyrido[4,3-b]indole. The average values of 6 samples of each tested product are shown in Table 3.

TABLE 3

| After test (hour) | Products of examples |||| 
|---|---|---|---|---|
| | Example 9 | Example 10 | Example 11 | Example 12 |
| | %, released 2,3,4,5-tetrahydro-2,8-dimethyl-5-[2-(6-methyl-3-pyridyl)ethyl]-1H-pyrido[4,3-b]indole ||||
| 2 | 22 | 15 | 20 | 16 |
| 4 | 33 | 25 | 36 | 24 |
| 6 | 42 | 35 | 49 | 30 |
| 8 | 52 | 43 | 59 | 36 |
| 12 | 62 | 58 | 72 | 48 |
| 18 | 74 | 72 | 85 | 57 |
| 24 | 82 | 83 | 87 | 66 |
| 30 | 83 | 86 | 90 | 75 |

It can be seen from the results in Table 3, although the components of the products of Examples 11 and 12 are the same, their release rates are different due to different process.

The granules of Examples 9-12 were independently mixed with purified talc powder and magnesium stearate, and filled in hard capsules so that each capsule contained 60 mg of 2,3,4,5-tetrahydro-2,8-dimethyl-5-[2-(6-methyl-3-pyridyl)ethyl]-1H-pyrido[4,3-b]indole. The obtained capsules were subjected to pharmacokinetic studies in rabbits, and blood samples were taken at: 1, 1.5, 2, 2.5, 3, 4, 6, 9, 12, 18, 24 and 36 hours after intragastric administration.

Using the capsules as above prepared in pharmacokinetic studies, at the middle point between 1 and 3 hours after taking blood samples, the peak plasma concentration of 2,3,4,5-tetrahydro-2,8-dimethyl-5-[2-(6-methyl-3-pyridyl)ethyl]-1H-pyrido[4,3-b]indole was 1-3 μg/ml, average Tmax was 1.65 h, average Cmax was 1.653 μg/ml, the plasma concentration after 24 h of the administration was still higher than the concentration after 4 h of oral administration of normal tablets in rabbits. When rabbits were subjected to intragastric administration of normal tablets containing 2,3,4,5-tetrahydro-2,8-dimethyl-5-[2-(6-methyl-3-pyridyl)ethyl]-1H-pyrido[4,3-b]indole, their plasma concentration was 1.3 μg/ml at 2 h, then dropped quickly within 4 h to 0.11 μg/ml, then only trace was observed (less than 0.1 μg/ml).

Based on the granules of Examples 9-12, the pharmacokinetic studies of intragastric administration of capsules containing 60 mg of 2,3,4,5-tetrahydro-2,8-dimethyl-5-[2-(6-methyl-3-pyridyl)ethyl]-1H-pyrido[4,3-b]indole show that the $W_{50}$ for 2,3,4,5-tetrahydro-2,8-dimethyl-5-[2-(6-methyl-3-pyridyl)ethyl]-1H-pyrido[4,3-b]indole is between 1-12 h, preferably 2-9 h, more preferably 2-5 h.

Example 13

Granules were prepared according to a method similar to that of Examples 9-12, except that the granules contained the following components:

| Tablet components | Weight (%) |
|---|---|
| 2,3,4,5-tetrahydro-2,8-dimethyl-5-[2-(6-methyl-3-pyridyl)ethyl]-1H-pyrido[4,3-b]indole | 55.0 |
| Hydrogenated vegetable oil | 44.7 |
| Polyethylene glycol 6000 | 0.3 |

Samples of the granules were then mixed with magnesium stearate and purified talc powder in two batches (see: batch 1 and batch 2 in Table 4), then the mixed mixture was tableted by a tableting device. The components of each unit dosage form have the following amounts.

TABLE 4

| Tablet components | Batch 1 (mg) | Batch 2 (mg) |
|---|---|---|
| 2,3,4,5-tetrahydro-2,8-dimethyl-5-[2-(6-methyl-3-pyridyl)ethyl]-1H-pyrido[4,3-b]indole | 60.00 | 60.00 |
| Hydrogenated vegetable oil | 48.77 | 48.77 |
| Polyethylene glycol | 0.33 | 0.33 |
| Sum | 109.1 | 109.1 |
| Magnesium stearate | 1.42 | 2.0 |
| Purified talc powder | 2.18 | 3.0 |

The dissolution of non tableted samples of the granules (each sample containing 60 mg of 2,3,4,5-tetrahydro-2,8-dimethyl-5-[2-(6-methyl-3-pyridyl)ethyl]-1H-pyrido[4,3-b]indole) was tested by the rotating basket method, and that of tablets was tested by Ph.Eur.Paddle method. The results are shown in Table 5:

TABLE 5

| After test start (hour) | Granules | Batch 1 of tablets | Batch 2 of tablets |
|---|---|---|---|
| | %, released 2,3,4,5-tetrahydro-2,8-dimethyl-5-[2-(6-methyl-3-pyridyl)ethyl]-1H-pyrido[4,3-b]indole |||
| 1 | 27 | 13 | 11 |
| 2 | 44 | 20 | 18 |
| 4 | 65 | 28 | 28 |
| 8 | 83 | 42 | 37 |
| 12 | 88 | 50 | 42 |
| 16 | 91 | 56 | 51 |
| 24 | 93 | 63 | Not recorded |
| 36 | 96 | 70 | Not recorded |

The above results showed that tableting decreased significantly the release rate of the active component.

Example 14

Granules were prepared according a method similar to that of Example 13, except that the granules contained the following components.

| Tablet components | Weight (%) |
|---|---|
| 2,3,4,5-tetrahydro-2,8-dimethyl-5-[2-(6-methyl-3-pyridyl)ethyl]-1H-pyrido[4,3-b]indole | 55.0 |
| Hydrogenated vegetable oil | 44.4 |
| Polyethylene glycol 6000 | 0.6 |

Samples of the granules were then mixed with magnesium stearate and purified talc powder in two batches (see: batch 3 and batch 4 in Table 6), then the mixed mixture was tableted by a tableting device. The components of each unit dosage form are in the following amounts.

TABLE 6

| Tablet components | Batch 3 of tablets (mg) | Batch 4 of tablets (mg) |
|---|---|---|
| 2,3,4,5-tetrahydro-2,8-dimethyl-5-[2-(6-methyl-3-pyridyl)ethyl]-1H-pyrido[4,3-b]indole | 60.00 | 60.00 |
| Hydrogenated vegetable oil | 48.44 | 48.44 |
| Polyethylene glycol 6000 | 0.655 | 0.655 |
| Sum | 109.1 | 109.1 |
| Poloxamer | 0 | 5.0 |
| Magnesium stearate | 1.42 | 2.0 |
| Purified talc powder | 2.18 | 3.0 |

The dissolution of non-tableted samples of the granules (each sample containing 60 mg of 2,3,4,5-tetrahydro-2,8-dimethyl-5-[2-(6-methyl-3-pyridyl)ethyl]-1H-pyrido[4,3-b]indole) was tested by the rotating basket method, and that of tablets was tested by Ph.Eur.Paddle method. The results are shown in Table 7:

TABLE 7

| After test start (hour) | Granules %, released 2,3,4,5-tetrahydro-2,8-dimethyl-5-[2-(6-methyl-3-pyridyl)ethyl]-1H-pyrido[4,3-b]indole | Batch 3 of tablets | Batch 4 of tablets |
|---|---|---|---|
| 1 | 55 | 16 | 20 |
| 2 | 75 | 25 | 29 |
| 4 | 89 | 33 | 38 |
| 8 | 95 | 47 | 54 |
| 12 | 98 | 55 | 62 |
| 16 | not recorded | 56 | 70 |
| 24 | not recorded | 67 | 78 |
| 36 | not recorded | not recorded | not recorded |

The above results showed that tableting decreased significantly the release rate of the active component. By comparing the release rates of tablet 3 and tablet 4, it can be seen that the use of surfactant (Poloxamer188) as tableting excipient can regulate release rate, the tablet 4 that contains the surfactant has a release rate 3 times higher than that of the tablet 3 that does not contain the surfactant.

Example 15

Granules were prepared according a method similar to that of Example 13, except that the granules contained the following components.

TABLE 8

| Tablet components | Weight (%) |
|---|---|
| 2,3,4,5-tetrahydro-2,8-dimethyl-5-[2-(6-methyl-3-pyridyl)ethyl]-1H-pyrido[4,3-b]indole | 30.0 |
| Hydrogenated vegetable oil | 69.95 |
| Polyethylene glycol 6000 | 0.05 |

Samples of the granules were then mixed with magnesium stearate and purified talc powder in one batch (see: batch 5 in Table 9), then the mixed mixture was tableted by a tableting device. The components of each unit dosage form are in the following amounts.

TABLE 9

| Tablet components | Batch 5 of tablets (mg) |
|---|---|
| 2,3,4,5-tetrahydro-2,8-dimethyl-5-[2-(6-methyl-3-pyridyl)ethyl]-1H-pyrido[4,3-b]indole | 30.00 |
| Hydrogenated vegetable oil | 69.95 |
| Polyethylene glycol | 0.05 |
| Sum | 100.0 |
| Magnesium stearate | 1.26 |
| Purified talc powder | 1.93 |

The dissolution of non tableted samples of the granules (each sample containing 30 mg of 2,3,4,5-tetrahydro-2,8-dimethyl-5-[2-(6-methyl-3-pyridyl)ethyl]-1H-pyrido[4,3-b]indole) was tested by the rotating basket method according to the ultraviolet spectrophotometry as set forth in Chinese Pharmacopoeia (2005 Edition, Part 2, Annexation IVA), and that of tablets was tested by Ph.Eur.Paddle method. The results are shown in Table 10:

TABLE 10

| After test start (hours) | Granules %, released 2,3,4,5-tetrahydro-2,8-dimethyl-5-[2-(6-methyl-3-pyridyl)ethyl]-1H-pyrido[4,3-b]indole | Batch 5 of tablets |
|---|---|---|
| 1 | 40.7 | 20.3 |
| 2 | 48.0 | 25.6 |
| 4 | 59.7 | 31.8 |
| 8 | 69.3 | 42.0 |
| 12 | 72.3 | 53.0 |
| 16 | 80.5 | 59.5 |
| 24 | 82.6 | 63.1 |
| 36 | 88.6 | 70.5 |

The above results showed that tableting decreased significantly the release rate of the active component during initial 8 hours.

Example 16

Granules were prepared according a method similar to that of Example 13, except that the granules contained the following components.

TABLE 11

| Tablet components | Weight (%) |
|---|---|
| 2,3,4,5-tetrahydro-2,8-dimethyl-5-[2-(6-methyl-3-pyridyl)ethyl]-1H-pyrido[4,3-b]indole | 15.0 |

TABLE 11-continued

| Tablet components | Weight (%) |
|---|---|
| Hydrogenated vegetable oil | 74.95 |
| Polyethylene glycol 6000 | 0.05 |

Samples of the granules were then mixed with magnesium stearate and purified talc powder in two batches (see: batch 6 and batch 7 in Table 12), then the mixed mixture was tableted by a tableting device. The components of each unit dosage form are in the following amounts.

TABLE 12

| Tablet component technical solution | Batch 6 of tablets (mg) | Batch 7 of tablets (mg) |
|---|---|---|
| 2,3,4,5-tetrahydro-2,8-dimethyl-5-[2-(6-methyl-3-pyridyl)ethyl]-1H-pyrido[4,3-b]indole | 15.00 | 15.00 |
| hydrogenated vegetable oil | 84.95 | 84.95 |
| polyethylene glycol | 0.05 | 0.05 |
| Sum | 100.0 | 100.0 |
| Magnesium stearate | 1.30 | 1.83 |
| Purified talc powder | 1.99 | 2.75 |

The dissolution of non-tableted samples of the granules (each sample containing 15 mg of 2,3,4,5-tetrahydro-2,8-dimethyl-5-[2-(6-methyl-3-pyridyl)ethyl]-1H-pyrido[4,3-b]indole) was tested by the rotating basket method according to the ultraviolet spectrophotometry as set forth in Chinese Pharmacopoeia (2005 Edition, Part 2, Annexation IV A), and that of tablets was tested by Ph. Eur. Paddle method. The results are shown in Table 13:

TABLE 13

| After test start (hour) | Granules | Batch 6 of tablets | Batch 7 of tablets |
|---|---|---|---|
| | %, released 2,3,4,5-tetrahydro-2,8-dimethyl-5-[2-(6-methyl-3-pyridyl)ethyl]-1H-pyrido[4,3-b]indole | | |
| 1 | 36.0 | 18.0 | 22.0 |
| 2 | 48.4 | 24.0 | 30.6 |
| 4 | 77.5 | 34.0 | 39.2 |
| 8 | 84.1 | 45.2 | 56.0 |
| 12 | 91.1 | 54.8 | 65.0 |
| 16 | 98.0 | 62.3 | 68.5 |
| 24 | not recorded | 70.2 | 77.6 |
| 36 | not recorded | not recorded | not recorded |

The above results showed that tableting decreased significantly the release rate of the active component.

What is claimed is:

1. A sustained-release granule consisting of:
a. the compound of formula I of 30.0 wt %

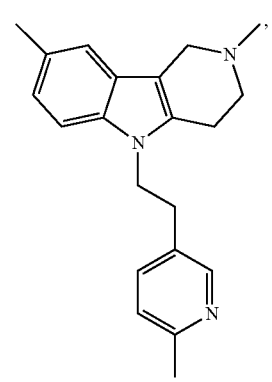

Formula I b. hydrogenated vegetable oil of 69.95 wt %, c. polyethylene glycol 6000 of 0.05 wt %.

2. A sustained-release tablet consisting of:
(i) sustained-release granules consisting of:
a. the compound of Formula I of 30.0 wt %

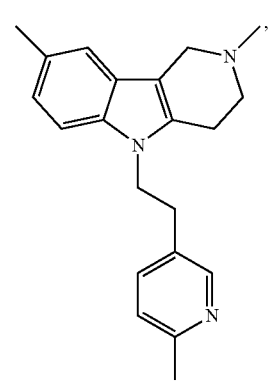

Formula I b. hydrogenated vegetable oil of 69.95 wt %, c. polyethylene glycol 6000 of 0.05 wt %; and (ii) a tablet excipient selected from the group consisting of poloxamer, magnesium stearate, talc, and combinations thereof.

3. A sustained-release granule consisting of:
a. the compound of formula I of 15.0 wt %

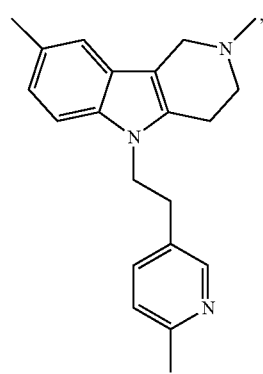

Formula I b. hydrogenated vegetable oil of 84.95 wt %, c. polyethylene glycol 6000 of 0.05 wt %.

4. A sustained-release tablet consisting of:
(i) sustained-release granules consisting of:
a. the compound of Formula I of 15.0 wt. %

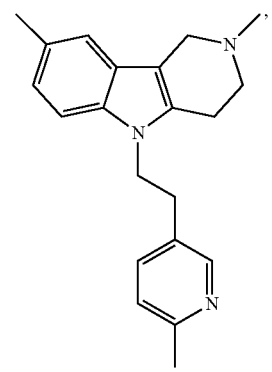

Formula I b. hydrogenated vegetable oil of 84.95 wt %,
c. polyethylene glycol 6000 of 0.05 wt. %; and
(ii) a tablet excipient selected from the group consisting of poloxamer, magnesium stearate, talc, and combinations thereof.

* * * * *